United States Patent
Berger et al.

(10) Patent No.: US 9,241,756 B2
(45) Date of Patent: Jan. 26, 2016

(54) REAL-TIME PREDICTION OF STEAM-POP EVENTS DURING ABLATION

(71) Applicant: BIOSENSE WEBSTER (ISRAEL), LTD., Yokneam (IL)

(72) Inventors: Abraham Berger, Givatayim (IL); Meir Bar-Tal, Haifa (IL); Avri Hazan, Givatayim (IL); Daniel Osadchy, Haifa (IL)

(73) Assignee: BIOSENSE WEBSTER (ISRAEL) LTD. (IL)

(*) Notice: Subject to any disclaimer, the term of this patent is extended or adjusted under 35 U.S.C. 154(b) by 169 days.

(21) Appl. No.: 13/932,397

(22) Filed: Jul. 1, 2013

(65) Prior Publication Data
US 2015/0005758 A1 Jan. 1, 2015

(51) Int. Cl.
*A61B 18/12* (2006.01)
*A61B 19/00* (2006.01)
*A61B 18/14* (2006.01)
*A61N 1/362* (2006.01)
*A61B 17/00* (2006.01)
*A61B 18/00* (2006.01)

(52) U.S. Cl.
CPC ............ *A61B 18/1233* (2013.01); *A61B 19/50* (2013.01); *A61B 18/1492* (2013.01); *A61B 2017/00318* (2013.01); *A61B 2018/00577* (2013.01); *A61B 2018/00702* (2013.01); *A61B 2018/00791* (2013.01); *A61B 2018/00839* (2013.01); *A61B 2018/00875* (2013.01); *A61B 2019/2253* (2013.01); *A61B 2019/462* (2013.01); *A61B 2019/504* (2013.01); *A61B 2217/007* (2013.01); *A61B 2218/002* (2013.01); *A61N 1/362* (2013.01)

(58) Field of Classification Search
CPC ............. A61B 19/50; A61B 2019/501; A61B 2018/00351; A61B 2018/00648; A61B 2018/00666; A61B 2018/00702; A61B 2018/00791; A61B 2018/00875; A61B 2018/008908; A61B 2018/00904
See application file for complete search history.

(56) References Cited

U.S. PATENT DOCUMENTS

| | | | | |
|---|---|---|---|---|
| 5,733,281 A | * | 3/1998 | Nardella | 606/38 |
| 6,709,432 B2 | * | 3/2004 | Ferek-Patric | 606/41 |
| 8,628,473 B2 | * | 1/2014 | Sliwa et al. | 600/439 |
| 8,641,705 B2 | * | 2/2014 | Leo et al. | 606/34 |
| 2008/0097220 A1 | * | 4/2008 | Lieber et al. | 600/475 |
| 2008/0177258 A1 | * | 7/2008 | Govari et al. | 606/41 |
| 2009/0287205 A1 | | 11/2009 | Ingle | |

(Continued)

FOREIGN PATENT DOCUMENTS

| EP | 2 364 664 A1 | 9/2011 |
|---|---|---|
| EP | 2 094 150 B1 | 12/2012 |

OTHER PUBLICATIONS

Pending U.S. Appl. No. 13/465,103, filed on May 7, 2012.

(Continued)

*Primary Examiner* — Ronald Hupczey, Jr.
(74) *Attorney, Agent, or Firm* — Louis J. Capezzuto

(57) ABSTRACT

A method for performing a medical procedure, includes, coupling a probe to tissue in an organ of a patient. Ablation energy is applied to the tissue using the probe. A model of an evolution of steam pressure in the tissue, caused by the ablation energy, as a function of time is estimated. Based on the model, an occurrence time of a steam pop event caused by the steam pressure is predicted, and the predicted occurrence time of the steam pop event is indicated to an operator.

21 Claims, 5 Drawing Sheets

(56) References Cited

U.S. PATENT DOCUMENTS

2011/0130648 A1    6/2011  Beeckler et al.
2011/0144524 A1*   6/2011  Fish et al. .................. 600/547
2011/0224664 A1*   9/2011  Bar-Tal et al. .............. 606/33
2014/0358038 A1*  12/2014  Byrd et al. .................. 600/586

OTHER PUBLICATIONS

EP Search Report 14 17 5030 Dated Nov. 27, 2014.

\* cited by examiner

REAL-TIME PREDICTION OF STEAM-POP EVENTS DURING ABLATION

FIELD OF THE INVENTION

The present invention relates generally to invasive medical treatment, and particularly to methods and systems for predicting steam pop events during ablation.

BACKGROUND OF THE INVENTION

Minimally-invasive intracardiac ablation is the treatment of choice for various types of arrhythmias. To perform such treatment, the physician typically inserts a catheter through the vascular system into the heart, brings the distal end of the catheter into contact with myocardial tissue in areas of abnormal electrical activity, and then energizes one or more electrodes at or near the distal end in order to create tissue necrosis.

A number of systems for intracardiac ablation therapy are commercially available, such as the CARTO™ system offered by Biosense Webster Inc. (Diamond Bar, Calif.). CARTO tracks the position and operating parameters of the distal end of the catheter and displays this information electronically on a three-dimensional (3D) anatomical map of the heart. CARTO enables the system operator to electronically tag locations that have been ablated on the map and thus to keep track of the progress of the procedure.

U.S. Patent Application Publication 2009/0287205, whose disclosure is incorporated herein by reference, describes a system for controllably delivering ablation energy to tissue. The system includes an ablation device operable to supply ablation energy to body tissue causing bubbles to form in the tissue, an ultrasound transducer configured to detect energy spontaneously emitted by collapsing or shrinking bubbles that are resonating in the tissue, and a control element operably coupled to the ablation device and the ultrasound transducer element, the control element being configured to adjust the ablation energy supplied to the tissue in response to the energy detected by the ultrasound transducer to prevent tissue popping caused by bubble expansion.

U.S. Patent Application Publication 2011/0224664 and European Patent Application Publication EP 2364664, whose disclosures are incorporated herein by reference, describe a method for ablating tissue in an organ inside a body of a subject. The method includes bringing a probe inside the body into a position in contact with the tissue to be ablated, and measuring one or more local parameters at the position using the probe prior to ablating the tissue. A map of the organ is displayed, showing, based on the one or more local parameters, a predicted extent of ablation of the tissue to be achieved for a given dosage of energy applied at the position using the probe. The given dosage of energy is applied to ablate the tissue using the probe, and an actual extent of the ablation at the position is measured using the probe subsequent to ablating the tissue. The measured actual extent of the ablation is displayed on the map for comparison with the predicted extent.

European Patent EP 2094150, whose disclosure is incorporated herein by reference, describes a method for monitoring formation of steam pocket during ablation, wherein a measured reflectance spectral intensity (MRSI) versus time is analyzed. The method includes delivering light to tissue, and measuring the reflectance spectral intensity of the tissue, wherein observation is made as to whether the MRSI initially increases in a specified time period followed by a decrease at a specified rate in the MRSI. If there is no decrease in the MRSI, then delivery of ablation energy to tissue continues. However, if there is a decrease in the MRSI within a specified time and at a specified rate, then the method infers the formation of a steam pocket and decreases or discontinues the delivery of ablative energy to tissue.

SUMMARY OF THE INVENTION

An embodiment of the present invention provides a method for performing a medical procedure, including coupling a probe to tissue in an organ of a patient. Ablation energy is applied to the tissue using the probe. A model of an evolution of steam pressure in the tissue, caused by the ablation energy, as a function of time, is estimated. Based on the model, an occurrence time of a steam pop event caused by the steam pressure is predicted, and the predicted occurrence time of the steam pop event is indicated to an operator.

In some embodiments, estimating the model includes estimating an evolution of temperature in the tissue, caused by the ablation energy, as a function of time. In other embodiments, estimating the model includes estimating a penetration depth of the probe into the tissue, and calculating the model based on the penetration depth and the ablation energy. In yet other embodiments, estimating the penetration depth includes measuring multiple values of temperature and impedance of the tissue, and estimating the penetration depth based on the measured values.

In an embodiment, estimating the model includes estimating a function curve of the tissue pressure as a function of time, and predicting the occurrence time of the steam pop event includes identifying an intersection time between the function curve and a predefined threshold, and deriving the occurrence time from the intersection time. In another embodiment, indicating the predicted occurrence time includes indicating to the operator a length of time remaining until the steam pop event. In yet another embodiment, the method further includes modifying application of the ablation energy in response to the predicted occurrence time of the steam pop event.

In some embodiments, estimating the model includes identifying a hottest region of the tissue in a vicinity of the probe, and assessing the evolution of the steam pressure at the hottest region. In other embodiments, estimating the model includes evaluating in real-time a finite-element heat transfer model of a vicinity of the probe.

There is additionally provided, in accordance with an embodiment of the present invention, apparatus for performing a medical procedure, including, an invasive probe and a processor which is coupled to the probe. The probe is configured to be coupled to tissue in an organ of a patient, and to apply ablation energy to the tissue. The processor is configured to estimate a model of an evolution of steam pressure in the tissue, caused by the ablation energy, as a function of time, to predict, based on the model, an occurrence time of a steam pop event caused by the steam pressure, and to indicate the predicted occurrence time of the steam pop event to an operator.

There is also provided, in accordance with an embodiment of the present invention, a computer software product, including a non-transitory computer-readable medium in which program instructions are stored, which instructions, when read by a processor that is coupled to an invasive probe for applying ablation energy to tissue in an organ to which the probe is coupled, cause the processor to estimate a model of an evolution of a steam pressure in the tissue, caused by the ablation energy, as a function of time, to predict, based on the model, an occurrence time of a steam pop event caused by the steam pressure, and to indicate the predicted occurrence time of the steam pop event to an operator.

The present invention will be more fully understood from the following detailed description of the embodiments thereof, taken together with the drawings in which:

DETAILED DESCRIPTION OF EMBODIMENTS

Overview

Figure 1A:
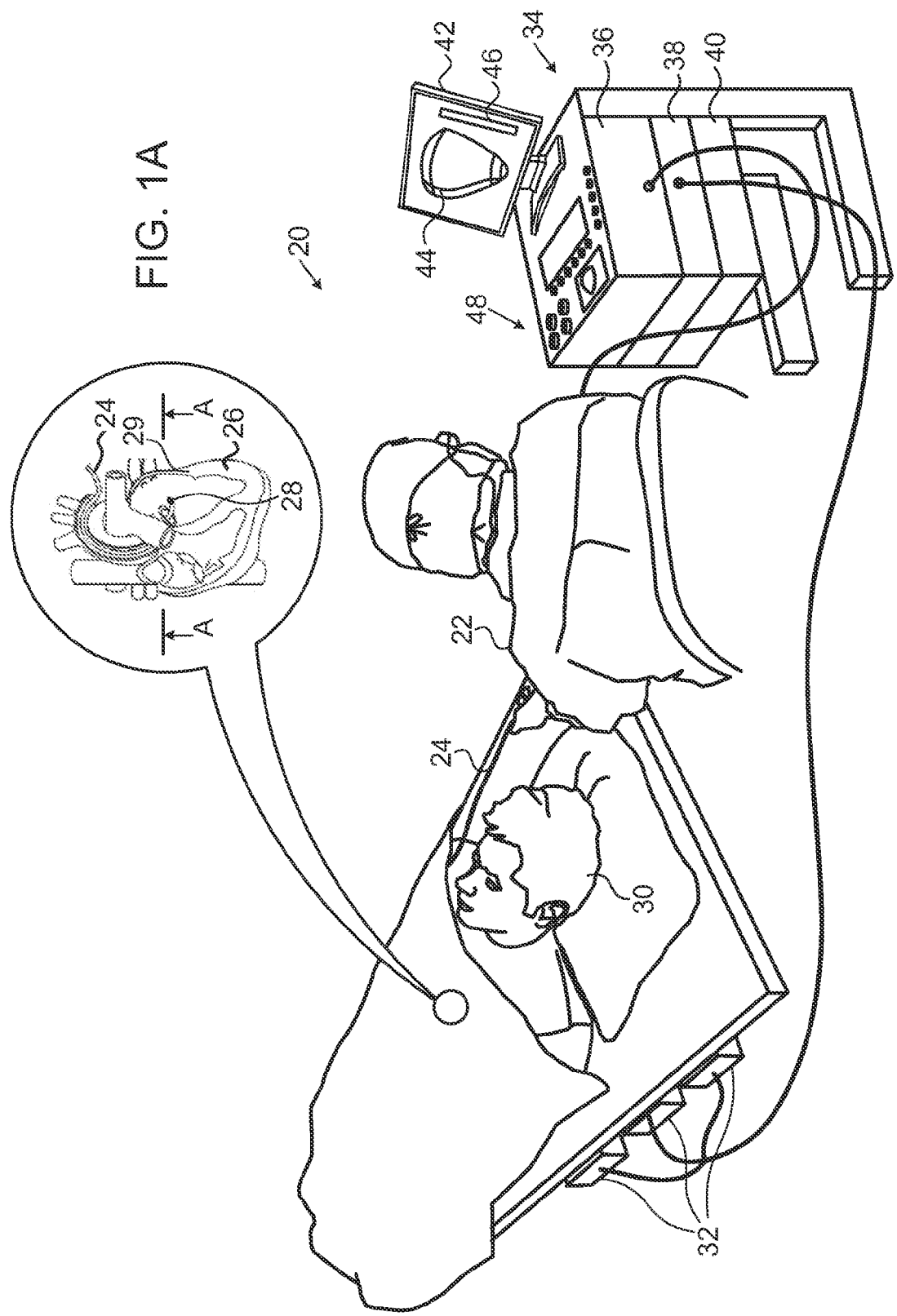
FIG. 1A is a schematic pictorial illustration of a system for intracardiac ablation, in accordance with an embodiment of the invention.

In some catheter-based treatment systems, such as the above-mentioned CARTO system, a physician conducting an ablation procedure inserts the catheter via the vascular system of the patient, to bring the distal tip of the catheter in contact with the tissue to be ablated. The physician then applies RF energy to the tissue via the catheter to create a lesion or necrosis in the tissue.

Tissue overheating is an undesirable side effect of applying RF energy to the tissue that may result in the formation of steam bubbles in the tissue. The hottest region of the tissue in the vicinity of the catheter is referred to as a hot-spot region. Typically, the hot-spot resides a few mm (e.g. about 1-2 mm) beneath the catheter tip. The tissue at the hot-spot has the highest risk of suffering from overheating. As steam pressure inside the bubbles evolves and builds up over time, reaching an excessive pressure level may cause bubbles to explode or collapse, resulting in tissue rupture. Moreover, the crater shaped damage formed in the myocardium disturbs blood flow and increases the risk of thrombus creation due to flow perturbations. The phenomenon of an exploding or collapsing steam bubble is referred to as a steam pop event.

Embodiments of the present invention that are described herein provide improved methods and systems for predicting the occurrence time of a steam pop event during the ablation procedure. The occurrence time (e.g., the time remaining until the expected steam pop event) is typically predicted in real time, so as to enable alerting the physician and/or taking responsive measures to avoid steam pop.

In some embodiments, tissue temperature and impedance measurements acquired in the probe, together with the ablation current, are used for evaluating a real-time model that predicts the hot-spot temperature as a function of time. In an example embodiment, the depth of the probe tip inside the tissue is first estimated using impedance and force measurements. The tip penetration depth is re-estimated until a match is found between temperature and impedance values calculated by a finite element model, and actual measurements.

The estimated tip depth and the ablation current are used to estimate the real-time model, so as to predict the evolution of steam pressure at the ablated tissue as a function of time. The estimated model serves to predict the occurrence time of an imminent steam pop event. In some embodiments, the estimated model comprises a temperature and/or pressure curve function, and the predicted occurrence time is derived from an intersection point of the model curve and a predefined temperature or pressure threshold.

The predicted occurrence time of the steam pop event is indicated to the physician or operator who carries out the ablation procedure. In some embodiments, the indication comprises, in addition to a numerical presentation of the predicted time, a presentation of the model curve on a display screen. Alternatively or additionally, the indication may comprise an audible indication such as a sound whose amplitude and/or frequency increases as time approaches the predicted occurrence time.

Using the indication of the expected imminent occurrence time of a steam pop event, the physician may take various actions, in advance, to reduce the risk for actual occurrence of such events. For example, the physician may reduce or even stop the ablation current to reduce the amount of energy applied to the tissue. Alternatively or additionally, the physician may reposition the probe tip to control the tip depth inside the tissue. Further alternatively or additionally, in case the ablation is conducted using an irrigated catheter, the physician may reduce the risk for steam pop events by controlling the irrigation rate. In alternative embodiments, the responsive action is taken automatically.

The finite element model and the real-time model are continuously updated during the ablation procedure, in order to maintain updated and accurate models under changing conditions created, for example, by heart beats and respiration operations of the patient.

Although the embodiments described below relate specifically to performance of intracardiac ablation, using a catheter of suitable design, the principles of the present invention may similarly be applied in other sorts of treatments, which may be applied to the heart or to other organs, using either catheters or other suitable types of invasive probes.

System Description

FIG. 1A is a schematic, pictorial illustration of a system 20 for intracardiac ablation, in accordance with an embodiment of the present invention. System 20 may be based, for example, on the above-mentioned CARTO system, with suitable additions to the system software. System comprises a probe, such as a catheter 24, and a control console 34. In the embodiment described hereinbelow, catheter 24 is used in ablating sites of arrhythmias in one or more chambers of a heart 26 of a patient 30. In some embodiments, catheter 24 comprises an irrigated catheter. Alternatively, catheter 24 or other suitable probes may be used, mutatis mutandis, for other therapeutic purposes in the heart or in other body organs.

An operator 22, such as a cardiologist, inserts catheter 24 through the vascular system of patient 30 so that the distal end of the catheter enters a chamber of heart 26. Operator 22 advances the catheter so that an electrode 28 at the distal tip of the catheter engages endocardial tissue at desired ablation sites. Catheter 24 is typically connected by a suitable connector at its proximal end to console 34, and specifically to a radio frequency (RF) generator 36, which generates RF energy for transmission via catheter 24 to electrode 28. Operator 22 actuates RF generator 36 to ablate tissue at suspected sites of arrhythmia in the heart. Electrical current applied to RF generator 36 controls the output power level generated.

In this pictured embodiment, system 20 uses magnetic position sensing to determine position coordinates of the distal end of catheter 24 inside heart 26. For this purpose, a driver circuit 38 in console 34 drives field generators 32 to generate magnetic fields within the body of patient 30. Typically, field generators 32 comprise coils, which are placed below the patient's torso at fixed, known positions. These coils generate magnetic fields in a predefined working volume that contains heart 26. A magnetic field sensor (not shown) within the distal end of catheter 24 generates electrical signals in response to these magnetic fields. A signal processor 40 processes these signals in order to determine the position coordinates of the distal end of catheter 24, typically including both location and orientation coordinates. This method of position sensing is implemented in the above-mentioned CARTO system and is well known in the art. Alternatively or additionally, system 20 may use other methods of position sensing that are known in the art, such as ultrasonic or electrical impedance-based methods.

In addition, catheter 24 may comprise a force sensor (not shown) in its distal end, for measuring the contact force between the catheter tip and a wall 29 of heart 26. The Smart-Touch™ catheter developed by Biosense Webster Inc. for the CARTO system offers this sort of capability. A catheter of this sort is described, for example, in U.S. Patent Application Publication 2011/0130648, whose disclosure is incorporated herein by reference. The force measurement is useful, for example, in ensuring that electrode 28 is in sufficiently firm contact with the heart wall to effectively transfer RF energy and ablate the heart tissue. As another example, in response to a suitable indication, operator 22 may reduce the catheter contact force in order to reduce the risk of overheating that may create a steam pop event.

Processor 40 in console 34 typically comprises a general-purpose computer processor, with suitable front end and interface circuits for receiving signals from catheter 24 and for controlling and receiving inputs from the other components of console 34. Processor 40 may be programmed in software to carry out the functions that are described herein. The software may be downloaded to processor 40 in electronic form, over a network, for example, or it may be provided, alternatively or additionally, on tangible, non-transitory media, such as optical, magnetic or electronic memory media. Further alternatively or additionally, some or all of the functions of processor 40 may be carried out by dedicated or programmable digital hardware components.

Based on the signals received from catheter 24 and other components of system 20, processor 40 drives a display 42 to present operator 22 with a three-dimensional (3D) map 44 of heart 26. The map may indicate cardiac electrophysiological activity measured by catheter 24, as well as providing visual feedback regarding the position of the catheter in the patient's body and status information and guidance regarding the procedure that is in progress. Other parameters that may be measured by catheter 24 and by other elements of system 20, delivered to processor 40, and shown on display 42 may include, for example, contact force between the catheter and heart tissue, electrical impedance between the ablation site and one or more points on the patient's skin, local temperature, and RF power delivered through the catheter.

Figure 1B:
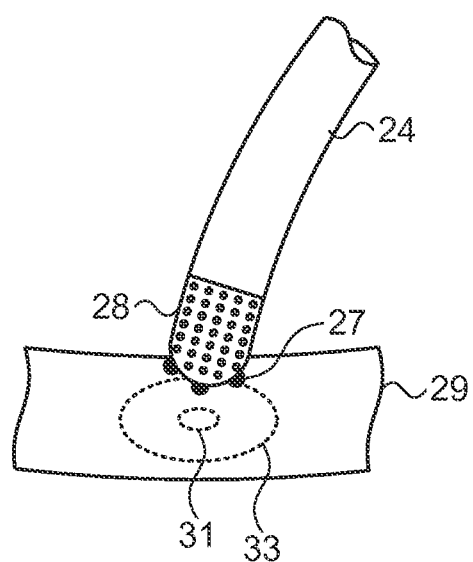
FIG. 1B is a schematic pictorial illustration of a catheter applying intracardiac ablation, in accordance with an embodiment of the present invention.

FIG. 1B is a schematic pictorial illustration of a cross section view along line A-A of FIG. 1A, in accordance with an embodiment of the present invention. FIG. 1B depicts catheter 24 whose tip is in contact with wall 29 of heart 26 at the ablated site. The catheter tip comprises an electrode 28 and sensors 27 for measuring the tissue interface temperature and impedance. System 20 uses catheter 24 to measure temperature of a hot-spot 31, as well as temperature and impedance values at a wider measurement region 33 that includes the hot-spot. Region 33 of the tissue is additionally part of a larger region that is referred to as a temperature domain as described further below. A catheter comprising sensors and electrodes for measuring tissue temperature and impedance is described, for example, in U.S. Patent Application Publication 2011/0224664 and in European Patent Application Publication EP 2364664 cited above.

Referring back to FIG. 1A, upon receiving measured/configured parameters, Processor 40 estimates a real-time model of the hot-spot temperature and pressure evolution in hot-spot 31 as a function of time. Based on the estimated model, processor 40 predicts an occurrence time of a steam pop event and presents a respective indication/alert 46 on display 42. Operator 22 may set configuration values, such as temperature or pressure threshold values using user interface controls 48 and on-screen menus.

Although FIGS. 1A and 1B show a particular system configuration and application environment, the principles of the present invention may similarly be applied in other therapeutic applications using not only catheters, but also probes of other types, both in the heart and in other body organs and regions.

Predicting the Time Occurrence of a Steam Pop Event

Figure 2:
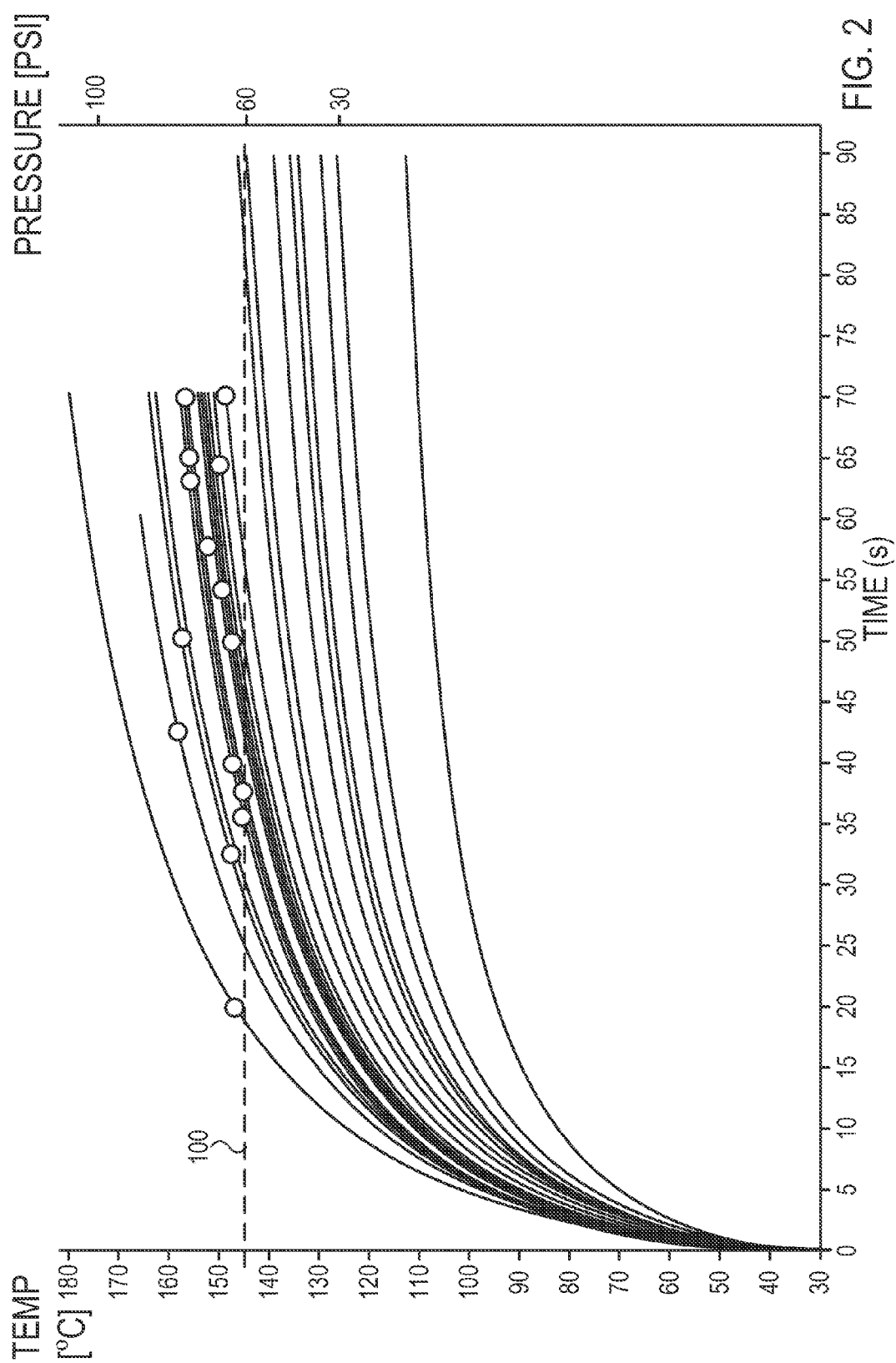
FIG. 2 is a graph showing calculated hot spot temperature and pressure values based on experimental measurements of tissue interface temperature during ablation, in accordance with an embodiment of the present invention.

FIG. 2 is a graph showing calculated hot spot temperature and pressure values based on experimental measurements of tissue interface temperature during ablation, in accordance with an embodiment of the present invention. The figure summarizes ablation experiments on animal subjects, conducted in June, 2012, at the Rambam medical center, Haifa, Israel. FIG. 2 depicts a horizontal time axis in units of seconds, a left vertical temperature axis in units of Celsius degrees, and a right vertical pressure axis in units of pounds per square inch (PSI). A horizontal threshold line 100 denotes both temperature and pressure thresholds of about 145 degrees Celsius and 60 PSI respectively.

In FIG. 2, each curve depicts the evolution of the hot-spot temperature over time during a respective ablation procedure. Typically, at stable ablation conditions such as catheter position and depth in tissue, contact force, RF power level, and irrigation rate, the hot-spot temperature rises during the ablation process. Each curve in FIG. 2 represents ablation that is performed at different conditions. For curves that never pass threshold 100, the ablation conditions limit the temperature level under about 145 degrees Celsius. Factors that may limit the temperature are, for example, low RF power and poor contact force between the catheter tip and the tissue. For other curves, however, the ablation conditions allow rapid temperature rise, up to a level higher than threshold 100.

A circle mark attached to curves that pass threshold 100 denotes a steam pop event. The experimental data demonstrates that the probability for the occurrence of a steam pop event is very high when the hot-spot temperature rises above 145 degrees (and correspondingly 60 PSI). On the other hand, when the temperature evolves to levels below 145 degrees Celsius a steam pop event is very rare and typically does not occur.

Thus, by controlling the ablation hot-spot temperature/pressure to levels below threshold 100, it is possible to significantly reduce the risk for the occurrence of seam pop events and related medical complications. Moreover, the time at which the hot-spot temperature crosses threshold 100 is highly indicative of the occurrence time of steam pop.

The specific temperature and pressure values, e.g., the value of threshold 100, should be regarded as example values. In alternative embodiments, any other suitable temperature and pressure values can be used. In particular, the numerical value of threshold 100 may be different. As noted above, the experimental data shown in FIG. 2 was measured on animal subjects. When applying the disclosed techniques to human patients, the numerical values may change. The general phenomenon, i.e., a pressure/temperature threshold that reliably distinguishes between very low probability of steam pop and very high probability of steam pop, is expected to remain.

Figure 3:
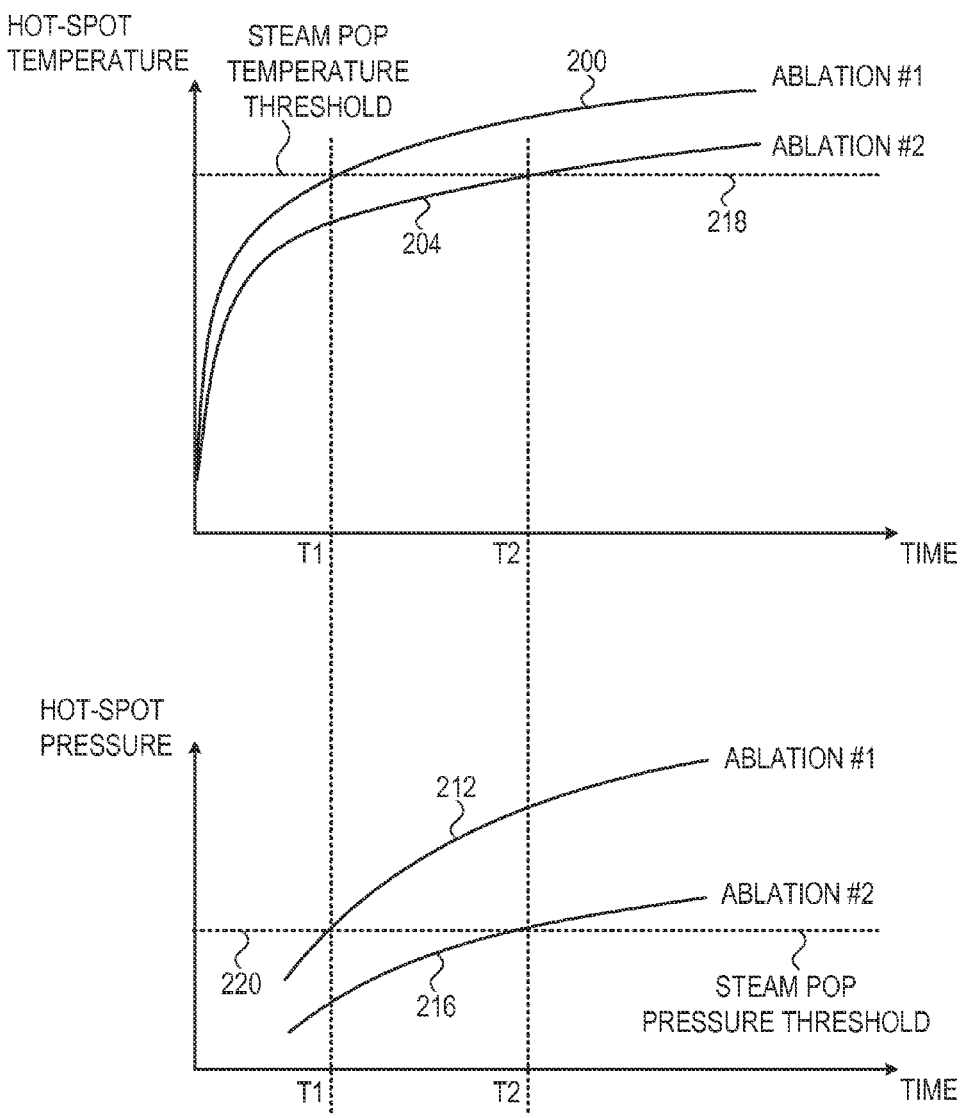
FIG. 3 is a graph showing tissue temperature and pressure evolution during ablation, in accordance with an embodiment of the present invention.

FIG. 3 is a graph showing tissue temperature and pressure evolution during ablation, in accordance with an embodiment of the present invention. In the figure, ABLATION #1 and ABLATION #2 denote first and second ablation procedures that are performed under different conditions. Curves 200 and 204 and similarly curves 212 and 216 depict temperature and pressure evolution during the first and second ablation procedures, respectively.

As depicted, the conditions at the first ablation procedure allow faster temperature and pressure rise at the tissue hot-spot with comparison to the second ablation procedure. Faster curve rise may result, for example, if the RF power delivered to the tissue during ABLATION #1 is higher, or if catheter 24 engages the tissue with firmer contact resulting in dipper deeper tip penetration into the tissue (and higher energy flow applied to the tissue). Irrigation rate is another factor that may affect the temperature and pressure rising rate.

As known from thermodynamics theory, the Clausius-Clapeyron equations define an exponential relationship between boiling vapor pressure and temperature as given by an expression derived from the relationship: $P=\exp\{A-B/T\}$, wherein P denotes pressure, T denotes the hot-spot temperature, and A and B are constants that depend mainly on thermal properties of the involved substances such as the heat of vaporization property. Therefore, pressure points on curves 212 and 216 in FIG. 3 are related to respective temperature points on curves 200 and 204 via the Clausius-Clapeyron equations.

Horizontal lines 218 and 220 represent temperature and pressure threshold levels. The thresholds divide the temperature and pressure levels at the hot-spot into two zones such that for points above the threshold the probability of steam pop events is very high, whereas for points below the threshold the probability of steam pop events is typically very low.

Based on the experimental results described with reference to FIG. 2 above, the temperature/pressure thresholds should be set to 145 degrees Celsius and 60 PSI respectively. In alternative embodiments, however, any other suitable threshold levels may be selected. As noted above, as the results in FIG. 2 are based on animal subjects, other threshold levels may be more adequate for human patients. As another example, ablation to different organs may result in different temperature/pressure evolution process and therefore may require different threshold levels. Temperature and pressure thresholds may be configured as constant values in the software run by processor 40, or may be manually configured by operator 22 prior to starting the ablation procedure.

T1 and T2 in FIG. 3, denote time instances in which a temperature/pressure curve crosses respective threshold 218 or 220. In the example of FIG. 3, T1<T2 since curves 200 and 212 rise faster than respective curves 204 and 216. Thus, when the ablation duration exceeds T1 for ABLATION #1 or T2 for ABLATION #2, the risk for steam pop occurrence increases significantly. Typical ablation time frame ranges between 20 to 90 seconds. By indicating T1 or T2 to operator 22 as soon as the ablation starts, the operator can take suitable actions, in advance, to reduce the risk of steam pop occurrences. According to practical experience of the inventors, the disclosed models and techniques enable to predict T1 or T2 within the first 2-3 seconds of the ablation procedure.

As noted above, hot-spot temperatures above threshold 218 are likely to cause steam pop occurrence with high probability. The hot spot is often located several mm below the surface, and therefore its temperature cannot be measured directly by the temperature sensor(s) in the catheter. Instead, in some embodiments processor 40 estimates the temperature of hot-spot 31 by evaluating (in real-time) a finite-element heat transfer model of the catheter and tissue environment (i.e., the temperature domain including region 33 in FIG. 1B). The boundary conditions for the model comprise the measured temperatures (by one or more sensors 27 in the catheter), the estimated tip depth, and the ablation current.

Processor 40 may additionally incorporate the influence of irrigation by setting a convection boundary condition on the internal tip surfaces of the probe, including the temperature of the relatively cold saline (whose temperature is usually about 28 degrees Celsius). The convection coefficient may be pre-calculated using, for example, a computational fluid dynamic (CFD) model.

Since steam pop events are created by excessive pressure inside bubbles formed in the tissue, and since there is a one-to-one relationship between pressure and temperature (e.g., according to the Clausius-Clapeyron equations mentioned above), the estimated hot-spot temperature can be used for reliably predicting a steam pop event.

Therefore, in some embodiments, steam pop events can be predicted based on pressure measurements, temperature measurements, or both. In the context of the present patent application and in the claims, the phrase "estimating a model that predicts evolution of pressure" may also refer to models that estimate the tissue temperature, and predict steam pop from the estimated temperature without explicitly calculating the estimated pressure.

Figure 4:
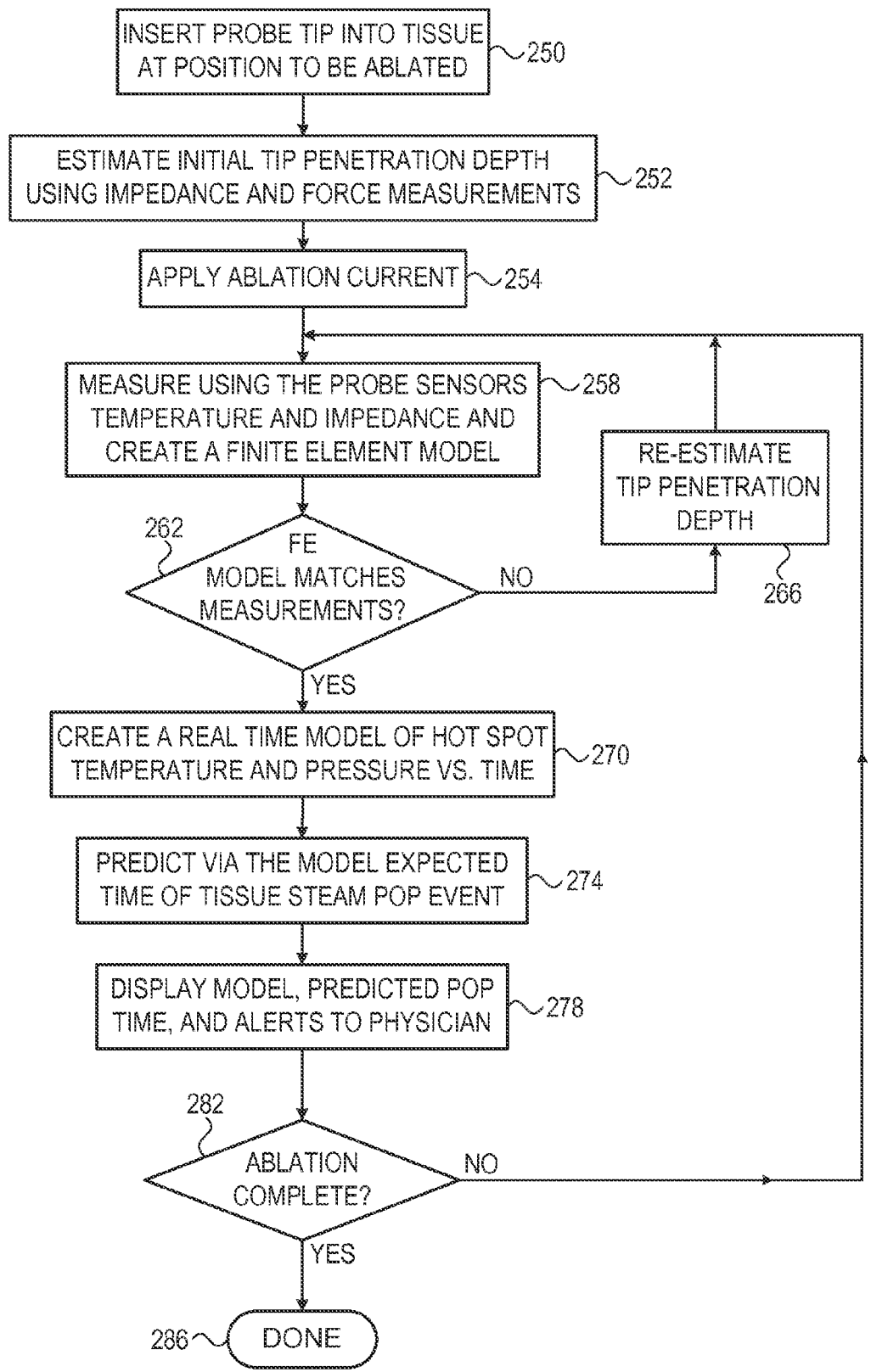
FIG. 4 is a flow chart that schematically illustrates a method for predicting the occurrence time of a steam pop event, in accordance with an embodiment of the present invention.

FIG. 4 is a flow chart that schematically illustrates a method for predicting the time occurrence of a steam pop event, in accordance with an embodiment of the present invention. The method begins with operator 22 inserting catheter 24 into the tissue to be ablated at a probe positioning step 250. Operator 22 may use any suitable method to select an ablation site within the tissue. For example, in heart ablation, operator 22 may select to ablate sites of arrhythmias as known in the art. Following probe positioning, processor 40 estimates the initial penetration depth of the probe tip into the tissue, at an initial depth estimation step 252. Processor 40 estimates the initial penetration depth using impedance measurements, and possibly temperature and/or force measurements.

Operator 22 then activates RF generator 36 at a current application step 254. The RF power level generated by RF generator 36 is controlled by the current level applied to the generator. Energy created by RF generator 36 is delivered via probe 24 to the tissue at the site of ablation. Typically, as RF energy is applied to the tissue, probe 24 performs temperature, impedance and force measurements that are delivered to processor 40.

Processor 40 uses the estimated tip depth, as well as temperature and impedance measurements to create a finite element (FE) model at a FE model creation step 258. The FE model comprises calculated temperature and impedance values at multiple sub-regions of a 3D region that is referred to as a temperature domain. The temperature domain typically comprises a region of the tissue, e.g., region 33 and hot-spot 32 in FIG. 1B, the catheter tip and sensors, and a region in close vicinity of the tissue wherein liquids such as blood and irrigation saline may be present. Note that sensors of the probe tip reside in some of the sub-regions of FE model.

Processor 40 compares the calculated temperature and impedance values of the FE model to actual measurements of the probe sensors at a model comparison step 262. In case there is no match at step 262, processor 40 re-estimates the tip penetration depth at a re-estimation step 266 and loops back to step 258. The loop of re-estimation of the penetration depth (step 266) and adjusting the FE model (step 258) continues until processor 40 finds a match at step 262, and proceeds to create a real-time model of the predicted hot-spot temperature and pressure evolution as a function of time at a real-time model creation step 270. The model is based at least on the probe penetration depth (i.e., the "free parameter" of the model) estimated at step 252 and or 266, and on the ablation current used to activate RF generator 36. The model typically comprises a predicted evolution curve of the temperature and/or pressure at the hot-spot. Alternatively, the model may comprise a table of temperature/pressure and time points. Further alternatively, the model may comprise any other suitable form, such as a mathematical formula.

Based on the model and on predefined temperature/pressure thresholds, processor 40 predicts an expected time occurrence of a steam pop event at a time prediction step 274. The predicted time may be derived from the intersection point between the model curve and a respective temperature/pressure threshold.

Processor 40 sends indication regarding the expected steam pop event to be presented on display 42 at a display indication step 278. Typically, the indication comprises audiovisual indications. For example, processor 40 can present the curves of the real-time model as well as the predefined thresholds. Alternatively or additionally, the indication may comprise a numerical presentation of the predicted time as calculated at step 274, or a length of time remaining until the steam pop event. Further alternatively or additionally, the indication may comprise an audible alert, such as (but not limited to) an alternate beep sound whose amplitude and/or frequency increases as time approaches the expected time of steam pop event. In some embodiments, processor 40 may present additional aiding information to operator 22. For example, processor 40 may continuously display a heart map 44, probe position relative to the heart chamber and wall, the penetration depth of the probe within the tissue, the amount of force the probe applies upon the tissue, and instantaneous hot-spot temperature and/or pressure measurements.

Operator 22 checks if ablation is concluded for the current site at a completion check step 282. Operator 22 may use any suitable method to decide on ablation conclusion. For example, operator 22 may decide to terminate the ablation if the amount of energy (e.g., the product of the RF power and time duration) applied to the tissue exceeds a predefined threshold. Alternatively or additionally, operator 22 may decide on ablation termination by consulting any suitable information presented on display 42 during the ablation process. Further alternatively or additionally, processor 40 may automatically decide on ablation termination using, for example, methods that are described in U.S. patent application Ser. No. 13/465,103, filed May 7, 2012, whose disclosure is incorporated herein by reference. In case the ablation at step 282 is concluded, the method terminates at a termination step 286. Otherwise, processor 40 loops back to step 258 to re-adjust the FE model in case deviations to the model have occurred. Factors that may cause FE model deviations include, for example, tissue-probe relative motion created by heart beats and respiration operations of patient 30. Note that adjusting the FE model at step 258 may be followed by respective updates to the real-time model at step 270, to the predicted occurrence time of the steam pop event at step 274, and to the alerts presented at step 278.

During the ablation procedure, operator 22 may take actions responsively to the indications presented at step 278, or to any other indications presented on display 42, in order to reduce the risk of a steam pop occurrence. For example, operator 22 may adjust the current applied to RF generator 36 to control the energy dosage applied to the tissue. As another example, if the real-time model of step 270 indicates a slow temperature/pressure evolution, the operator may increase the current applied to RF generator 36. On the other hand, if system 20 indicates an imminent steam pop event, operator 20 may reduce or even completely shut down the current applied to RF generator 36.

Alternatively or additionally, operator 22 may adjust the position or penetration depth of catheter 24 into the tissue, or even temporarily remove the catheter from being in contact with the tissue. The operator may apply increased force upon the catheter to insert it deeply into the tissue if the prediction model indicates a slow rising temperature/pressure curve. In case, however, the model indicates an imminent occurrence of a steam pop event, operator 22 may partially or completely remove catheter 24 from the tissue. Further alternatively or additionally, operator 22 may control irrigation rate, and/or any other suitable means that may affect temperature/pressure evolution rate, responsively to the model indication.

It would be appreciated that the operator may respond with various actions in parallel to reduce the risk for a stem pop event.

In alternative embodiments, some of the actions that are manually taken by operator 22 may be automated by processor 40. For example, processor 40 may automatically control ablation current to RF generator 36 and/or irrigation rate. As another example, in a system 20 that supports electro-mechanical maneuvering of the catheter, processor 40 may automatically reposition catheter 24 within the tissue.

The configuration described in FIG. 4 above is an example configuration, which is chosen purely for the sake of conceptual clarity. In alternative embodiments, any other suitable configuration can also be used.

It will be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A method for performing a medical procedure, comprising:
   coupling a probe to tissue in an organ of a patient;
   applying ablation energy to the tissue using the probe;
   estimating a model of an evolution of steam pressure in the tissue, caused by the ablation energy, as a function of time;

predicting, based on the model, an occurrence time of a steam pop event caused by the steam pressure; and indicating the predicted occurrence time of the steam pop event to an operator, wherein estimating the model comprises estimating a penetration depth of the probe into the tissue, and calculating the model based on the penetration depth and the ablation energy.

2. The method according to claim 1, wherein estimating the model comprises estimating an evolution of temperature in the tissue, caused by the ablation energy, as a function of time.

3. The method according to claim 1, wherein estimating the penetration depth comprises measuring multiple values of temperature and impedance of the tissue, and estimating the penetration depth based on the measured values.

4. The method according to claim 1, and comprising modifying application of the ablation energy in response to the predicted occurrence time of the steam pop event.

5. The method according to claim 1, wherein estimating the model comprises identifying a hottest region of the tissue in a vicinity of the probe, and assessing the evolution of the steam pressure at the hottest region.

6. Apparatus for performing a medical procedure, comprising:

an invasive probe, which is configured to be coupled to tissue in an organ of a patient, and to apply ablation energy to the tissue; and a processor, which is coupled to the probe and is configured to estimate a model of an evolution of steam pressure in the tissue, caused by the ablation energy, as a function of time, to predict, based on the model, an occurrence time of a steam pop event caused by the steam pressure, and to indicate the predicted occurrence time of the steam pop event to an operator, wherein the processor is configured to estimate the model by estimating a penetration depth of the probe into the tissue, and to calculate the model based on the penetration depth and the ablation energy.

7. The apparatus according to claim 6, wherein the processor is configured to estimate the model by estimating an evolution of temperature in the tissue, caused by the ablation energy, as a function of time.

8. The apparatus according to claim 6, wherein the processor is configured to estimate the penetration depth by measuring multiple values of temperature and impedance of the tissue and estimating the penetration depth based on the measured values.

9. The apparatus according to claim 6, wherein the processor is configured to modify application of the ablation energy in response to the predicted occurrence time of the steam pop event.

10. The apparatus according to claim 6, wherein the processor is configured by the operator to modify application of the ablation energy in response to the predicted occurrence time of the steam pop event.

11. The apparatus according to claim 6, wherein the processor is configured to estimate the model by identifying a hottest region of the tissue in a vicinity of the probe, and to assess the evolution of the steam pressure at the hottest region.

12. A computer software product, comprising a non-transitory computer-readable medium in which program instructions are stored, which instructions, when read by a processor that is coupled to an invasive probe for applying ablation energy to tissue in an organ to which the probe is coupled, cause the processor to estimate a model of an evolution of a steam pressure in the tissue, caused by the ablation energy, as a function of time, to predict, based on the model, an occurrence time of a steam pop event caused by the steam pressure, and to indicate the predicted occurrence time of the steam pop event to an operator, wherein the model is estimated by estimating a penetration depth of the probe into the tissue, and the model is calculated based on the penetration depth and the ablation energy.

13. A method for performing a medical procedure, comprising:

coupling a probe to tissue in an organ of a patient;
applying ablation energy to the tissue using the probe;
estimating a model of an evolution of steam pressure in the tissue, caused by the ablation energy, as a function of time;
predicting, based on the model, an occurrence time of a steam pop event caused by the steam pressure; and
indicating the predicted occurrence time of the steam pop event to an operator, wherein estimating the model comprises estimating a function curve of the tissue pressure as a function of time, and wherein predicting the occurrence time of the steam pop event comprises identifying an intersection time between the function curve and a predefined threshold, and deriving the occurrence time from the intersection time.

14. A method for performing a medical procedure, comprising:

coupling a probe to tissue in an organ of a patient;
applying ablation energy to the tissue using the probe;
estimating a model of an evolution of steam pressure in the tissue, caused by the ablation energy, as a function of time;
predicting, based on the model, an occurrence time of a steam pop event caused by the steam pressure; and
indicating the predicted occurrence time of the steam pop event to an operator, wherein indicating the predicted occurrence time comprises indicating to the operator a length of time remaining until the steam pop event.

15. A method for performing a medical procedure, comprising:

coupling a probe to tissue in an organ of a patient;
applying ablation energy to the tissue using the probe;
estimating a model of an evolution of steam pressure in the tissue, caused by the ablation energy, as a function of time;
predicting, based on the model, an occurrence time of a steam pop event caused by the steam pressure; and
indicating the predicted occurrence time of the steam pop event to an operator, wherein estimating the model comprises evaluating in real-time a finite-element heat transfer model of a vicinity of the probe.

16. Apparatus for performing a medical procedure, comprising:

an invasive probe, which is configured to be coupled to tissue in an organ of a patient, and to apply ablation energy to the tissue; and a processor, which is coupled to the probe and is configured to estimate a model of an evolution of steam pressure in the tissue, caused by the ablation energy, as a function of time, to predict, based on the model, an occurrence time of a steam pop event caused by the steam pressure, and to indicate the predicted occurrence time of the steam pop event to an operator, wherein the processor is configured to estimate the model by estimating a function curve of the tissue pressure as a function of time, and to predict the occurrence time of the steam pop event by identifying an intersection time between the function curve and a predefined threshold and deriving the occurrence time from the intersection time.

17. Apparatus for performing a medical procedure, comprising:
- an invasive probe, which is configured to be coupled to tissue in an organ of a patient, and to apply ablation energy to the tissue; and
- a processor, which is coupled to the probe and is configured to estimate a model of an evolution of steam pressure in the tissue, caused by the ablation energy, as a function of time, to predict, based on the model, an occurrence time of a steam pop event caused by the steam pressure, and to indicate the predicted occurrence time of the steam pop event to an operator, wherein the processor is configured to indicate the predicted occurrence time by indicating to the operator a length of time remaining until the steam pop event.

18. Apparatus for performing a medical procedure, comprising:
- an invasive probe, which is configured to be coupled to tissue in an organ of a patient, and to apply ablation energy to the tissue; and
- a processor, which is coupled to the probe and is configured to estimate a model of an evolution of steam pressure in the tissue, caused by the ablation energy, as a function of time, to predict, based on the model, an occurrence time of a steam pop event caused by the steam pressure, and to indicate the predicted occurrence time of the steam pop event to an operator, wherein the processor is configured to estimate the model by evaluating in real-time a finite-element heat transfer model of a vicinity of the probe.

19. A computer software product, comprising a non-transitory computer-readable medium in which program instructions are stored, which instructions, when read by a processor that is coupled to an invasive probe for applying ablation energy to tissue in an organ to which the probe is coupled, cause the processor to estimate a model of an evolution of a steam pressure in the tissue, caused by the ablation energy, as a function of time, to predict, based on the model, an occurrence time of a steam pop event caused by the steam pressure, and to indicate the predicted occurrence time of the steam pop event to an operator, the model being estimated by estimating a function curve of the tissue pressure as a function of time, and the occurrence time of the steam pop event being predicted by identifying an intersection time between the function curve and a predefined threshold and deriving the occurrence time from the intersection time.

20. A computer software product, comprising a non-transitory computer-readable medium in which program instructions are stored, which instructions, when read by a processor that is coupled to an invasive probe for applying ablation energy to tissue in an organ to which the probe is coupled, cause the processor to estimate a model of an evolution of a steam pressure in the tissue, caused by the ablation energy, as a function of time, to predict, based on the model, an occurrence time of a steam pop event caused by the steam pressure, and to indicate the predicted occurrence time of the steam pop event to an operator by indicating to the operator a length of time remaining until the steam pop event.

21. A computer software product, comprising a non-transitory computer-readable medium in which program instructions are stored, which instructions, when read by a processor that is coupled to an invasive probe for applying ablation energy to tissue in an organ to which the probe is coupled, cause the processor to estimate a model of an evolution of a steam pressure in the tissue, caused by the ablation energy, as a function of time, to predict, based on the model, an occurrence time of a steam pop event caused by the steam pressure, and to indicate the predicted occurrence time of the steam pop event to an operator, and estimating the model by evaluating in real-time a finite-element heat transfer model of a vicinity of the probe.

* * * * *